Figure 1:
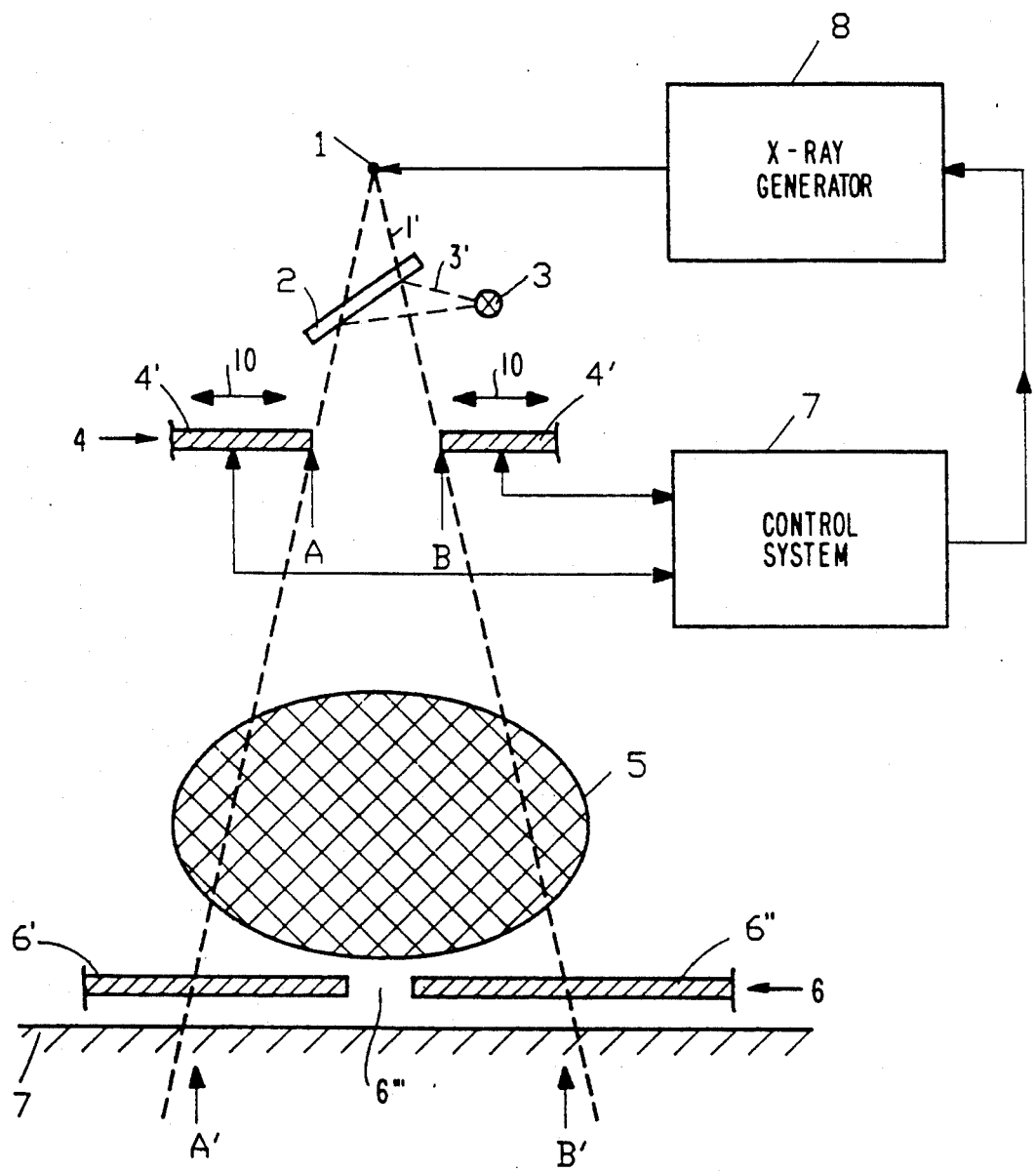

United States Patent [19]

Conrads et al.

[11] Patent Number: 5,136,627

[45] Date of Patent: Aug. 4, 1992

[54] SLIT DIAPHRAGM SYSTEM DEFINING X-RAY EXAMINATION ZONE WITH VISIBLE LIGHT AND FOR PASSING X-RAY RADIATION TO THE DEFINED ZONE

[75] Inventors: Norbert Conrads, Hauset, Belgium; Walter Hillen, Aachen-Walheim, Fed. Rep. of Germany

[73] Assignee: U.S. Philips Corporation, New York, N.Y.

[21] Appl. No.: 566,640

[22] Filed: Aug. 13, 1990

[30] Foreign Application Priority Data

Aug. 26, 1989 [DE] Fed. Rep. of Germany ....... 3928282

[51] Int. Cl.$^5$ ................................................ A61B 6/08
[52] U.S. Cl. ..................................... 378/206; 378/62; 378/146; 378/147; 378/152
[58] Field of Search .................... 378/62, 88, 206, 14, 378/145, 146, 156, 157, 41, 153, 152, 147

[56] References Cited

U.S. PATENT DOCUMENTS

| | | | |
|---|---|---|---|
| 3,629,594 | 12/1971 | Sandberg | 378/206 |
| 3,921,001 | 11/1975 | Edholm et al. | 378/206 |
| 4,060,733 | 11/1977 | Franke et al. | 378/206 |
| 4,167,675 | 9/1979 | Stödberg et al. | 378/206 |
| 4,419,764 | 12/1983 | Kinanen | 378/153 |
| 4,521,905 | 6/1985 | Hosokawa | 378/206 |
| 4,670,896 | 6/1987 | Klausz | 378/206 |
| 4,672,212 | 6/1987 | Brahme | 378/153 |
| 4,715,056 | 12/1987 | Vlasbloem et al. | 378/152 |
| 4,894,850 | 1/1990 | Frings et al. | 378/62 |
| 4,969,174 | 11/1990 | Scheid et al. | 378/146 |

Primary Examiner—Janice A. Howell
Assistant Examiner—Kim-Kwok Chu
Attorney, Agent, or Firm—William Squire

[57] ABSTRACT

At least one primary diaphragm comprises two elements displaceable so as to form a linear fan-shaped beam which is incident on an object to be examined. The elements form the slit-shaped aperture forming the fan beam in their normal X-ray beam forming position and are moveable to a respective, selectable limit position perpendicularly to the fan shaped beam in order to define and mark an examination zone greater in cross-section area than the fan beam with a light beam. Light incident on the examination zone is restricted by the diaphragm elements in their limit positions, thus marking the examination zone with the light beam. X-ray exposure of the object to be examined takes place only when the elements are between the two positions defining the examination zone of the primary diaphragm where its diaphragm elements occupy in their respective limit positions.

10 Claims, 2 Drawing Sheets

SLIT DIAPHRAGM SYSTEM DEFINING X-RAY EXAMINATION ZONE WITH VISIBLE LIGHT AND FOR PASSING X-RAY RADIATION TO THE DEFINED ZONE

BACKGROUND OF THE INVENTION

1. Field of the Invention

The invention relates to an X-ray exposure device, comprising an X-ray source and radiation detector including a slit diagram to form a fan-shaped radiation beam which is incident on an object to be examined.

2. Description of the Prior Art

In radiography it is generally desirable to mark the zone to be examined, i.e. the zone where an object to be examined is exposed to X-rays, prior to the exposure. The examination zone is generally so marked by coupling in light rays between the focus of the X-ray source and a stationary diaphragm, which light rays are confined by the diaphragm so as to define the examination zone in the plane of examination.

For slit radiography exposure techniques, however, this marking technique is not readily possible, because the primary diaphragm has a very narrow slit which forms the X-rays into a fan-shaped beam across the object to be examined.

Another possibility of applying the light for slit radiography exposure techniques couples light with mirrors located between the primary diaphragm and the object to be examined. An arrangement of this kind, however, has the drawback that the distance between the focus of the X-ray source and the primary diaphragm is thus inevitably reduced if the overall device is not to become too voluminous. The distance between the focus and the primary diaphragm, however, should be as large as possible in order to minimise the penumbral areas of the radiation beam in the examination plane. This is desirable in view of the need for suppression of scattered radiation of the primary beam transmission. Moreover, the coupling-in of light between the examination plane and the primary slit reduces the range for object positioning in the examination plane.

SUMMARY OF THE INVENTION

It is the object of the invention to construct an X-ray exposure device of the kind set forth so that coupling-in of a light field is possible while avoiding the described drawbacks.

This object is achieved in accordance with the invention in that the primary X-ray beam forming diaphragm comprises at least two diaphragm elements which form the slit-shaped aperture in their normal X-ray beam forming position and. The elements are moveable to a respective, selectable limit position, perpendicularly to the slit direction, in order to define an examination zone via a light beam. A light source projects light onto the object to be examined which projection is restricted by the diaphragm elements in their limit positions. This marks the examination zone. X-ray exposure of the object to be examined occurs only between the two elements limit positions of the primary diaphragm.

In this arrangement, the primary diaphragm also serves as usual for slit-radiographic exposure of the object to be examined in its normal X-ray beam forming position in which the two diaphragm elements are moved close to one another so as to form the slit-shaped aperture.

Before the X-ray examination operation, however, the two diaphragm elements are moved apart in a direction perpendicular to the X-ray beam forming slit-shaped aperture formed thereby. Above the primary diaphragm elements is a light source whose light beam incident on the object to be examined is limited by means of the two diaphragm elements. The diaphragm elements are moved sufficiently apart so that the desired examination zone is marked by the incident light passed by the so moved elements. The diaphragm elements in this position occupy their respective limit position.

After the examination zone has thus been defined by the light, the diaphragm elements are moved closer to their normal X-ray beam forming position again, so that they again form the slit-shaped aperture. During the exposure of the object to be examined to X-rays, the primary diaphragm is moved so that the object to be examined is linearly exposed to the X-rays. Such an exposure of the object to be examined, however, is performed only between the two positions of the primary diaphragm where its diaphragm elements occupy their respective limit position. This exposure to X-rays is thus started when the first diaphragm element has reached its limit position. Subsequently, both elements of the the primary diaphragm are moved further until the second diaphragm element has reached its limit position. The X-ray exposure is then terminated.

In the present arrangement no limitation exists as regards the dimension of the examination zone, because the range of operation of the elements between the primary diaphragm X-ray beam forming and the examination zone forming position remains unlimited. However, in a slit-radiographic X-ray exposure device coupling-in of a light field is still possible, as the examination zone is defined by the light and can be optically followed simply by selection of the limit position of the two diaphragm elements.

In further preferred embodiments in accordance with the invention this can be realised by moving the two diaphragm elements to their respective limit position either by hand or by way of a motor.

A further embodiment in accordance with the invention includes a control logic system which activates the X-ray source during an exposure only during the period of time in which the diaphragm elements of the primary diaphragm are situated between their respective limit positions.

The control logic system thus ensures that, in dependence on the selected limit positions, the object to be examined is exposed only in the defined examination zone. Depending on the construction of the X-ray exposure device, it can be ensured that in any case a maximum examination zone is covered by a corresponding displacement of the X-ray beam forming slit. In that case, however, the X-ray source is switched on only during the period of time in which the diaphragm elements of the primary diaphragm are situated between their respective limit positions.

Figure 2:
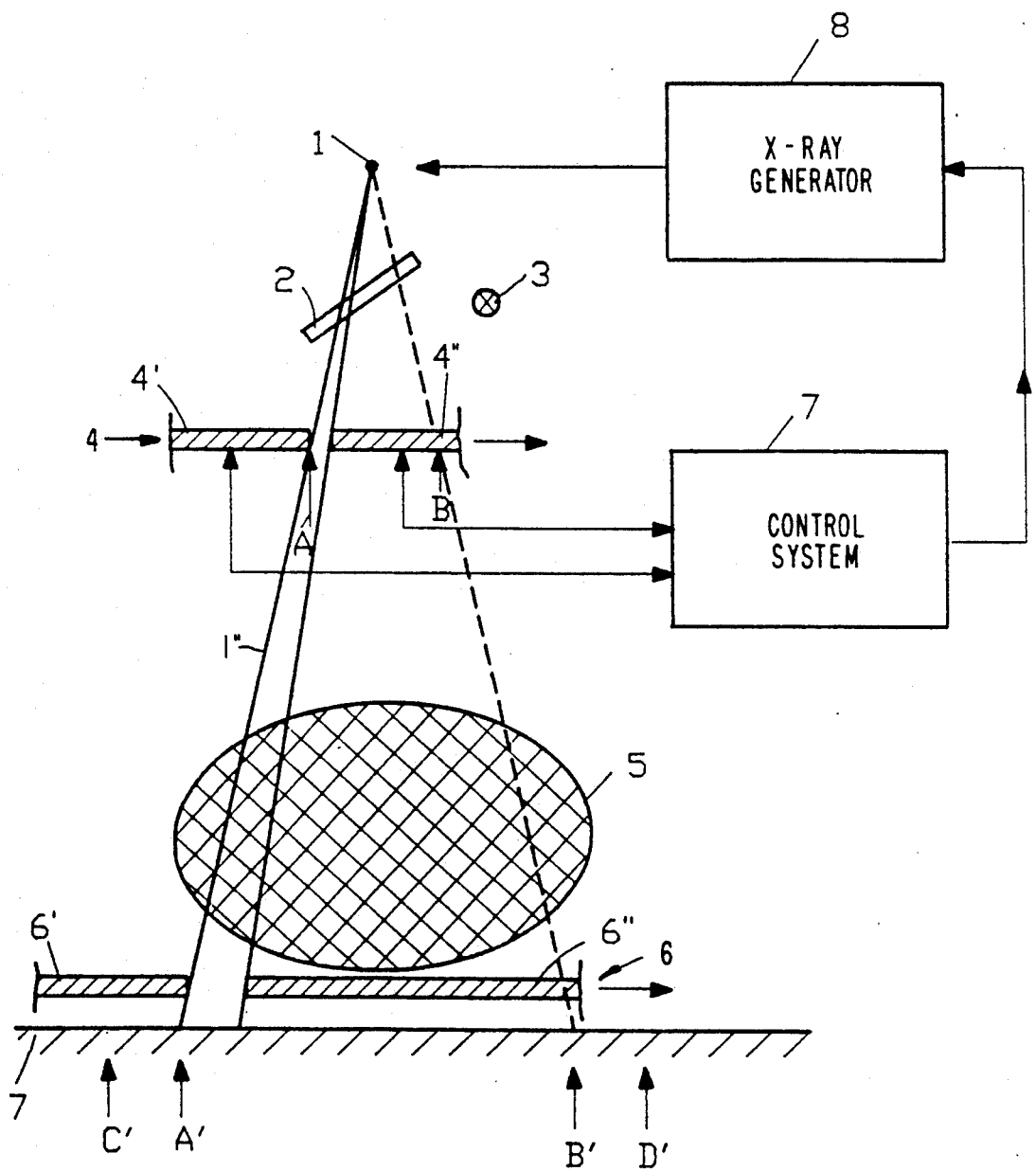

An embodiment in accordance with the invention will be described in detail hereinafter with reference to the drawing. Therein:

FIG. 1 diagrammatically shows the essential components of an X-ray exposure device, the diaphragm elements of the primary diaphragm being shown in their limit positions, and FIG. 2 shows the device of FIG. 1 during the X-ray exposure.

The reference numeral 1 in FIG. 1 denotes an X-ray source, for example an X-ray tube; in FIG. 1, however, only the focus wherefrom the X-rays emanate is shown. In the beam path 1' of the X-ray source 1 there is arranged a mirror 2 which is transparent to the X-rays emitted by the source 1 and which is capable of projecting light 31' from a laterally arranged light source 3 into the beam path 1'.

In the beam path 1' there is subsequently positioned a primary diaphragm 4 which comprises two diaphragm elements 4' and 4 each of which occupy a respective limit position. The limit positions are denoted by the arrows A and B in the Figure. The diaphragm elements 4' and 4 are only diagrammatically shown in the Figure, without their supports or motor drive.

In the beam path 1' there is indicated (diagrammatically) an object 5 to be examined. On a side of the object opposite diaphragm 4 there is arranged a secondary diaphragm 6 which consists of two diaphragm elements 6' and 6. The diaphragm elements 6' and 6 of the secondary diaphragm form a linear, slit-shaped aperture 6''' wherethrough X-rays are incident on an X-ray image detector 7 which is only diagrammatically indicated in the Figure and which may be, for example, an X-ray film or a pohotoconductor.

The two diaphragm elements 4' and 4'' of the primary diaphragm 4 can be displaced in directions 10 by way of a motor (in a manner not shown in the Figure), control being realised by means of a control logic system 7 which controls an X-ray generator 8 for operating the X-ray source 1.

In the embodiment of FIG. 1, the two diaphragm elements 4' and 4'' for defining the examination zone occupy a respective limit position. For defining the examination zone, the X-ray source 1 is switched off and the light source 3 is switched on (by means not shown). The light emitted by the light beam 3 source 3 is projected into the beam path by way of the mirror 2 and is incident laterally restricted by the two diaphragm elements 4' and 4'', on the object 5 to be examined or on the examination plane formed by the two secondary diaphragm elements 6'' and 6''. The incidence of light on the object 5 to be examined or on the examination plane marks the examination zone. At the plane level of the examination zone on detector 7 lateral boundaries A' and B' are formed which correspond to the limit positions A and B of the primary slit-diaphragm elements 4' and 4''.

The two primary slit-diaphragm elements 4' and 4'' may be movable to the limit position shown in FIG. 1 either by hand or by way of a motor.

In the representation of FIG. 2, showing the X-ray exposure position of the device of FIG. 1, the two diaphragm elements 4' and 4'' of the primary slit diaphragm 4 are shown in their normal X-ray beam forming position, i.e. the position in which they form a linear, slit-shaped aperture for X-ray exposure of the object to be examined.

During the X-ray exposure, the two diaphragm elements 4' and 4'' of the primary slit diaphragm 4 and the two diaphragm elements 6' and 6'' of the secondary slit diaphragm 6 are moved in synchronism with one another so that they remain aligned in one plane together with the focus 1 of the X-ray source to forming X-ray beam 1'' (solid lines).

During the X-ray exposure of the object 5 to be examined the control logic system 7 controls the X-ray generator 8, and hence the X-ray source 1, so that the object 5 to be examined is exposed only between the positions A' and B' which correspond to the limit positions A and B of the diaphragm elements 4' and 4'', of the primary slit diaphragm 4.

The mechanical displacement of the primary slit diaphragm 4 and the secondary slit diaphragm 6 can also be realised in a maximum examination zone, for example between the positions C' and D' in the plane of the secondary slit diaphragm 6. In that case, for example starting in the position C' in the secondary slit plane, the primary slit as well as the secondary slit are moved in synchronism, be it that initially the X-ray source is still switched off. It is only after the diaphragm element 4' of the primary slit diaphragm 4 has reached its limit position A that the X-ray source 1 is switched on. In that case X-rays are incident on the radiation detector 7 at the area of the arrow A' in the secondary slit plane. Subsequently, the diaphragm elements 4' and 4'' of the primary slit diaphragm 4 and the diaphragm elements 6' and 6'' are synchronously moved further until the diaphragm element 4'' reaches its limit position B. As soon as this is the case, the X-ray generator 8 is switched off by the control logic system 7 so that no further X-rays are emitted by the radiation source 1. The diaphragm elements 4' and 4'' of the primary slit diaphragm and 6' and 6'' of the secondary slit diaphragm can then be moved further, if necessary, to an extreme position D'.

Regardless of whether the diaphragm elements of the two diaphragms 4 and 6 are mechanically moved only in the desired examination zone or between extreme positions (for example, the positions C' and D' in accordance with FIG. 2), it is in any case important that the object to be examined is exposed only in the examination zone defined by the limit positions of the primary slit diaphragm elements 4' and 4'', i.e. the X-ray source may be activated only when the X-rays are incident on the object to be examined in this zone as defined by beam 1', FIG. 1.

It is to be noted that the movement of the primary slit diaphragm elements 4' and 4'' need not necessarily be linear as shown in the Figures; it may also be that the primary slit diaphragm elements pivot about the focus of the X-ray source 1 so that the slits of the primary diaphragm and the secondary diaphragm and the focus 1 of the X-ray source are aligned.

We claim:

1. An X-ray system for exposing an object to X-ray radiation comprising:
   a source of X-ray radiation;
   an X-ray radiation detector;
   a source of light radiation;
   a primary diaphragm comprising at least two diaphram elements, said elements having a first position forming a first slit aperture therebetween of a first transverse width for forming said X-ray radiation into a fan shaped beam extending linearly in a given direction, said beam for impinging on said object, said elements being displaceable in a direction transverse said given direction to a selectable spaced apart position forming a second aperture of a transverse width greater than the first aperture, radiation from said light source passing through said elements in the second position defining an examination zone on said object;
   means for causing said light radiation to pass through the aperture formed by said elements in the second position for marking the examination zone; and means for displacing the elements so that the first aperture is displaced in a range defined by the second aperture during exposure of the object by said X-ray radiation.

2. An X-ray exposure device as claimed in claim 1 including a deflection mirror arranged between the X-ray source and the primary diaphragm for coupling the light from the light source to said primary diaphragm.

3. An X-ray exposure device as claimed in claim 2 including means for manually adjusting the at least two diaphragm elements to their respective limit position defined by said range.

4. An X-ray exposure device as claimed in claim 1 including motor means for adjusting the two diaphragm elements to their respective limit position.

5. An X-ray exposure device as claimed in claim 3 including a control logic system which stores the limit positions of said elements defined by the second aperture and which logic system activates the X-ray source during an X-ray exposure only for the period of time during which the diaphragm elements of the primary diaphragm are present between their respective limit positions.

6. An X-ray exposure device as claimed in claim 4 including a control logic system which stores the limit positions of said elements defined by the second aperture and which logic system activates the X-ray source during an X-ray exposure only for the period of time during which the diaphragm elements of the primary diaphragm are present between their respective limit positions.

7. An X-ray exposure device as claimed in claim 5 including a control logic system which stores the limit positions of said elements defined by the second aperture and which logic system activates the X-ray source during an X-ray exposure only for the period of time during which the diaphragm elements of the primary diaphragm are present between their respective limit positions.

8. An X-ray system for exposing an object to X-ray radiation comprising:
 a source of X-ray radiation;
 an X-ray radiation detector secured for receiving said radiation passed through said object;
 a source of light radiation;
 a primary diaphragm comprising at least two movable diaphragm elements, said elements having a first position forming a first slit aperture therebetween of a first transverse width for forming said X-ray radiation into a fan shaped beam extending linearly in a given direction normal to said transverse width;
 means for selectively coupling the light from said light source to said diaphragm such that light from said source is formed by the diaphragm into a beam, said light beam defining a transverse area coincident with said X-ray radiation beam, said beams impinging on said object;
 means for moveably securing said elements so that they are displaceable in a direction transverse said given direction to a selectable spaced apart position forming a second aperture of a transverse width greater than the first aperture;
 means for causing said light to pass through the second aperture for defining and visually marking an examination zone on the object; and
 means for displacing the elements so that the first aperture is displaced in a range whose limits are defined by the position of the elements forming the second aperture during exposure of the object by said X-ray radiation.

9. An X-ray sysstem for exposing an object to X-ray radiation comprising:
 a source of X-ray radiation;
 an X-ray radiation detector secured for receiving said radiation;
 a source of light radiation;
 a primary diaphragm comprising at least two diaphragm elements, said elements having a first position forming a first slit aperture therebetween of a first transverse width for forming said X-ray radition into a fan shaped beam extending linearly in a given direction, said beam for impinging on said object, said elements being displaceable in a direction normal said given direction to a selectable spaced apart position forming a second aperture of a transverse width greater than the first transverse width;
 means for causing said light to pass through the second aperture for defining and marking an examination zone on said object;
 means for displacing the elements to form the first aperture; and
 means for displacing the elements forming said first aperture in unison to a limit position defined by the second aperture so that the first aperture is displaced in a range defined by the second aperture during exposure of the object by said X-ray radiation.

10. The system of claim 9 including electronic control means for causing said elements to form the first aperture and to displace said first aperture in said range.

* * * * *